United States Patent [19]

Granger et al.

[11] Patent Number: 5,448,823
[45] Date of Patent: * Sep. 12, 1995

[54] APPARATUS AND METHOD FOR SECURING SUTURES TO SURGICAL NEEDLES

[75] Inventors: Richard N. Granger, Huntington; Michael S. Kassim, Monroe, both of Conn.

[73] Assignee: United States Surgical Corporation, Norwalk, Conn.

[*] Notice: The portion of the term of this patent subsequent to Nov. 12, 2010 has been disclaimed.

[21] Appl. No.: 666,808

[22] Filed: Mar. 8, 1991

[51] Int. Cl.⁶ .............................................. B23P 11/02
[52] U.S. Cl. ...................................... 29/721; 29/447; 29/565; 29/DIG. 35
[58] Field of Search .................... 29/447, 235, 564.1, 29/565, 720, 721, 797, DIG. 13, DIG. 24, DIG. 35; 128/401; 156/423; 604/161; 606/222, 224, 227

[56] References Cited

U.S. PATENT DOCUMENTS

| | | | |
|---|---|---|---|
| 3,437,788 | 4/1969 | Lingley | 29/447 |
| 3,784,778 | 1/1974 | McPhersone et al. | 219/159 X |
| 4,418,453 | 12/1983 | Brown et al. | 29/447 X |
| 4,470,415 | 9/1984 | Wozniak | 29/447 X |
| 4,722,384 | 2/1988 | Matsutani . | |
| 4,834,637 | 5/1989 | Conta et al. | 156/423 X |
| 5,041,128 | 8/1991 | Korthoff | 606/224 |

FOREIGN PATENT DOCUMENTS 9101152.3 1/1990 Germany .

OTHER PUBLICATIONS

Document "Neelded Suture", File No. P.C. 7729, Jan. 2, 1991.

Primary Examiner—Joseph M. Gorski
Assistant Examiner—Peter Dungba Vo
Attorney, Agent, or Firm—Thomas R. Bremer; Peter G. Dilworth; Rocco S. Barrese

[57] ABSTRACT

An apparatus for manufacturing suture-needle assemblies in which the suture thread is connected to the needle shank through the provision of heat shrinkable tubing. The apparatus for securing the heat shrink tubing to the shank of the needle essentially comprises a needle holder, a heat source, a video camera and monitor device and means for insuring heating of the tubing only at the shank. An apparatus is also disclosed for securing the suture thread to the needle shank where the needle shank is already provided with the heat shrink tubing secured thereon. The apparatus for securing the suture thread to the needle shank includes a needle holder, a heat source, a heat cover to create a heating chamber, as well as video camera and monitor means to enlarge the image for an operator, as well as temperature regulating equipment.

38 Claims, 8 Drawing Sheets

APPARATUS AND METHOD FOR SECURING SUTURES TO SURGICAL NEEDLES

BACKGROUND OF THE INVENTION

1. Field of the Invention

The present invention relates to equipment for manufacturing surgical equipment, and more particularly to an apparatus for constructing surgical suture-needle assemblies which secures the suture to the needle shank to form the suture-needle assembly.

2. Discussion of the Prior Art

In the suture field, and in particular the suture-needle assembly industry, there are many known ways of attaching a suture to the needle to form the final surgical assembly. In this field, where the demand for suture-needle assemblies (hereinafter suture-needle assemblies will be referred to as simply "sutures") is ever increasing, the requirement for an efficient, high volume means for assembling sutures is a priority for suture manufacturers. In the prior art, devices for assembling sutures are varied depending on the construction of the needles to which the suture thread is attached.

Typically, many needles are provided with a pointed tip and a blunt shank end which generally includes a longitudinally directed bore hole for accepting therein a suture thread. After the thread is inserted into the bore hole, the shank is crimped or swaged about the thread to hold it in place. Other means of securing the thread within the bore of the needle shank include the use of adhesives or bonding agents to anchor the thread.

It has now become common to secure the thread to the needle shank in such a way so as to allow for the removal of the needle from the thread after the suturing operation is complete. In this manner, a sharp tug or pull on the needle separates the needle from the thread to eliminate the necessity for the surgeon to cut the thread after the suturing procedure is finished. In order to accomplish this, it has become known to apply the thread to the needle shank through the provision of a heat shrinkable tubing which is shrunk about both the shank end and the thread to hold the thread to the needle. After the suturing procedure is complete, the surgeon can then apply a sharp pull force to the needle which separates the thread from the needle by releasing the thread at the heat shrink tubing.

Due to the large volume of sutures manufactured to satisfy the demand in the field, it is necessary to provide an apparatus for assembling the sutures which is efficient and which can handle a high volume under strict quality control. In addition, it is necessary in many cases to protect the suture thread from degradation due to the heat which is applied to shrink the heat shrinkable tubing about the shank and the end of the suture thread. Many types of suture threads, in particular catgut, collagen, and many plastics such as polypropylene, will seriously degrade if the application of heat is prolonged or is applied at excessive temperatures. If the suture thread drys out, it may crack at the connection point, thus rendering the suture useless. On the other hand, inefficient heating will cause ineffective shrinking, thus rendering the connection weak and impractical.

The novel apparatus for securing suture threads to needle shanks to form suture-needle assemblies of the present invention obviates the disadvantages encountered in the prior art and provides an efficient means for constructing sutures at a high volume and with high quality control. The device of the present invention insures a connection between a needle shank and a suture thread which is of high integrity and which protects delicate suture threads from degradation during the securement process. Furthermore, the present invention allows for a high volume and efficient manufacturing process to meet the growing demand for sutures having a quick release feature.

SUMMARY OF THE INVENTION

The present invention provides a novel apparatus for attaching suture threads to needles to form surgical sutures which substantially reduces or eliminates the possibility of damage to the suture thread during the securing process. The apparatus secures the suture thread to the needles through the provision of heat shrink tubing which provides a strong connection while maintaining a quick release feature as required in the field. The apparatus provides for efficient manufacture of sutures while maintaining high quality at a high volume.

The apparatus of the present invention is actually a system for constructing sutures, in which at least two stations interact to apply the suture thread to the needle shank in a series of steps. Each station is manned with an operator who controls the securement operation at his individual station. The first station provides an apparatus for securing a small length of heat shrinkable tubing to the shank of a needle, while a second station provides an apparatus for securing the suture thread to the needle shank having the heat shrinkable tubing already positioned thereon. It is also contemplated that a single station be provided, in that a single operator oversees the connection of the suture thread to the needle shank in a single operative step. Furthermore, it is also contemplated that while the preferred steps of manufacture proceeds with the securing the heat shrink tubing to the shank of the needle and then the suture thread to the heat shrink tubing attached to the needle shank, it is also contemplated that the steps may be reversed, i.e., the heat shrink tubing be attached to the suture thread and then the needle shank be attached to the heat shrink tubing which is already attached to the suture thread.

The first station of the apparatus for securing the heat shrinkable tubing to the needle shank essentially consists of a holding device which holds the needle in place at the station. The apparatus is preferably set up at a work station or bench which allows an operator to sit at the station to control the securement process. The needle is secured in a clamping device which positions the shank end of the needle adjacent a heat source which applies the heat to shrink the heat shrinkable tubing about the shank. The heat source is directed to a controlled area so that only a portion of the heat shrink tubing is shrunk about the shank, thus allowing the opposite end of the heat shrink tubing to remain unaffected by the heat to maintain its original shape and dimensions for subsequently accepting the suture thread.

The station is provided with various control devices for controlling the temperature of the heat source and the duration of the application of the heat, and means are also provided for manipulating and holding the heat shrink tubing to the end of the shank during the heating process. Furthermore, a viewing device is provided for magnifying and enlarging a control work area to provide the operator with a magnified view to facilitate the manufacturing process.

In use, the operator secures a needle in the holder so that the shank end of the needle is positioned over the heat source. The operator positions a small length of heat shrinkable tubing over the shank of the needle and then applies pressure to the open end of the heat shrink tubing to maintain the tubing in place over the shank. This is preferably accomplished through the use of a piston which is pneumatically fired to abut the end of the heat shrink tubing to hold it in place over the shank. Alternately, a solenoid having a movable core may be used to urge the tubing over the shank. Due to the small size of the needle shank and the heat shrink tubing, the operator utilizes the magnification device, which is preferably a television camera which displays the control area on a video monitor, or a lens system such as a microscope which magnifies the working area. It is preferred that a positioning device such as a beveled trough be provided to align the tubing with the shank. The piston is then activated to urge the tubing over the shank. After the piston is moved into position to hold the heat shrink tubing in place, the operator activates the heat source which applies a controlled amount of heat in the vicinity of the shank end to shrink the heat shrink tubing only about the shank, leaving the end adjacent the piston in an unheated state to allow for the subsequent insertion of the suture thread for further securement. To insure only the localized heating, the needle holding device is preferably constructed of a material such as ceramic which serves as a heat sink.

In a first embodiment, the heat source is a stream of heated air which is concentrated by a nozzle and directed only at the end of the shank to prevent complete shrinking of the tubing along its entire length. In a second, preferred embodiment, the heat source is an electrode which contacts the needle in the vicinity of the shank to provide instantaneous contact heating to the shank which causes the shrink tubing to shrink about the shank from the inside outwardly. After the application of heat, the tubing is allowed to briefly cool before the piston is retracted and the holding means opened to release the needle with the heat shrink tubing attached to the shank. The operator then repeats this process on another needle.

While in the preferred embodiment a single needle undergoes the procedure, it is apparent that the device may be modified to accommodate several needles at a time.

Subsequent to the securement of the heat shrink tubing to the needle shank, the needles are moved to a second station where a second operator secures the suture thread to the heat shrink tubing which is on the shank. At this station, control means are also provided which control the temperature of the heat source and the duration of the heat applied. Viewing means are also provided which magnify the control area to assist the operator, and at this station the operator secures the needle to the apparatus so that the shank having the heat shrink tubing attached thereto is positioned within the vicinity of the heat source. After locking the needle in place, the operator inserts the suture thread into the open end of the heat shrink tubing which has not been shrunk, and after insertion activates the heat source. Preferably, prior to application of the heat source, a heat chamber is created through the provision of a sliding cover member which slides over the connection point between the suture thread and the heat shrink tubing to create a chamber for the application of a hot air stream to the heat shrink tubing. Preferably, the cover consists of a glass slide which allows the operator to view the work site. As the slide covers the work area, a hot air stream is applied which circulates about the tubing and shrinks the heat shrink tubing about the suture thread to secure the thread to the needle. After the short application of heat, the slide is retracted, the heat shrink tubing is allowed to briefly cool, and then the needle assembly is removed from the holder as a finished product. Again, while it is described that a single suture thread is attached to a needle at a time, it is obvious that several threads may be secured to needles simultaneously.

BRIEF DESCRIPTION OF THE DRAWINGS

The foregoing features of the present invention will become more readily apparent and may be understood by referring to the following detailed description of an illustrative embodiment of the apparatus for securing suture threads to surgical needles, taken in conjunction with the accompanying drawings, in which.

DETAILED DESCRIPTION OF THE PREFERRED EMBODIMENTS

Figure 1:
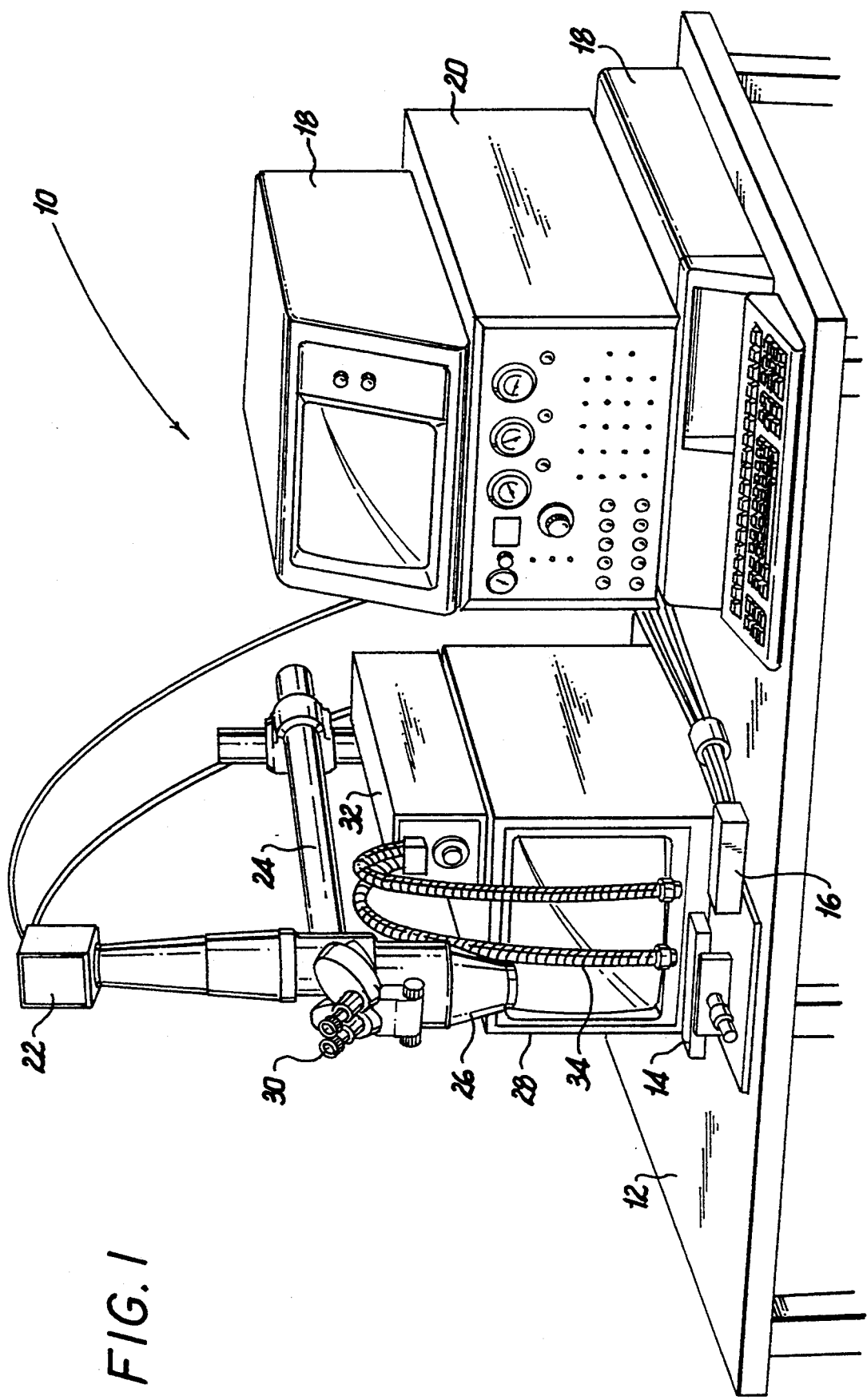
FIG. 1 illustrates a perspective view of a work station utilizing the preferred embodiment of the apparatus of the present invention.

Referring now in specific detail to the drawings, in which like reference numerals identify similar or identical elements throughout the several views, FIG. 1 shows a work station 10 for securing suture threads to surgical needles to form suture-needle assemblies according to the present invention. Work station 10 is to be manned by an operator and the station itself is set up at a bench or table 12 and includes the securing apparatus 14 of the present invention. A control connector 16 is provided which joins securing apparatus 14 to the control equipment shown on bench 12. The control equipment includes a computer terminal 18 having a conventional display monitor and disk drive as shown, and a control terminal 20 is connected to the computer terminal and is monitored and controlled by computer terminal 18.

A video camera 22 is provided which is secured to bracket 24 and positioned so that lens system 26 is located above the work area of securing apparatus 14. Lens system 26 and video camera 22 magnify and enlarge the work area at securing apparatus 14 and display the enlarged image on monitor 28 to allow the operator to better view the work apparatus. Alternately, instead of camera 22, viewing device 30 may be provided to allow the operator to view the magnified image directly. In order to clarify the image, a light source 32 is provided having telescopic arms 34 which illuminate the work area at securing apparatus 14.

Figure 2:
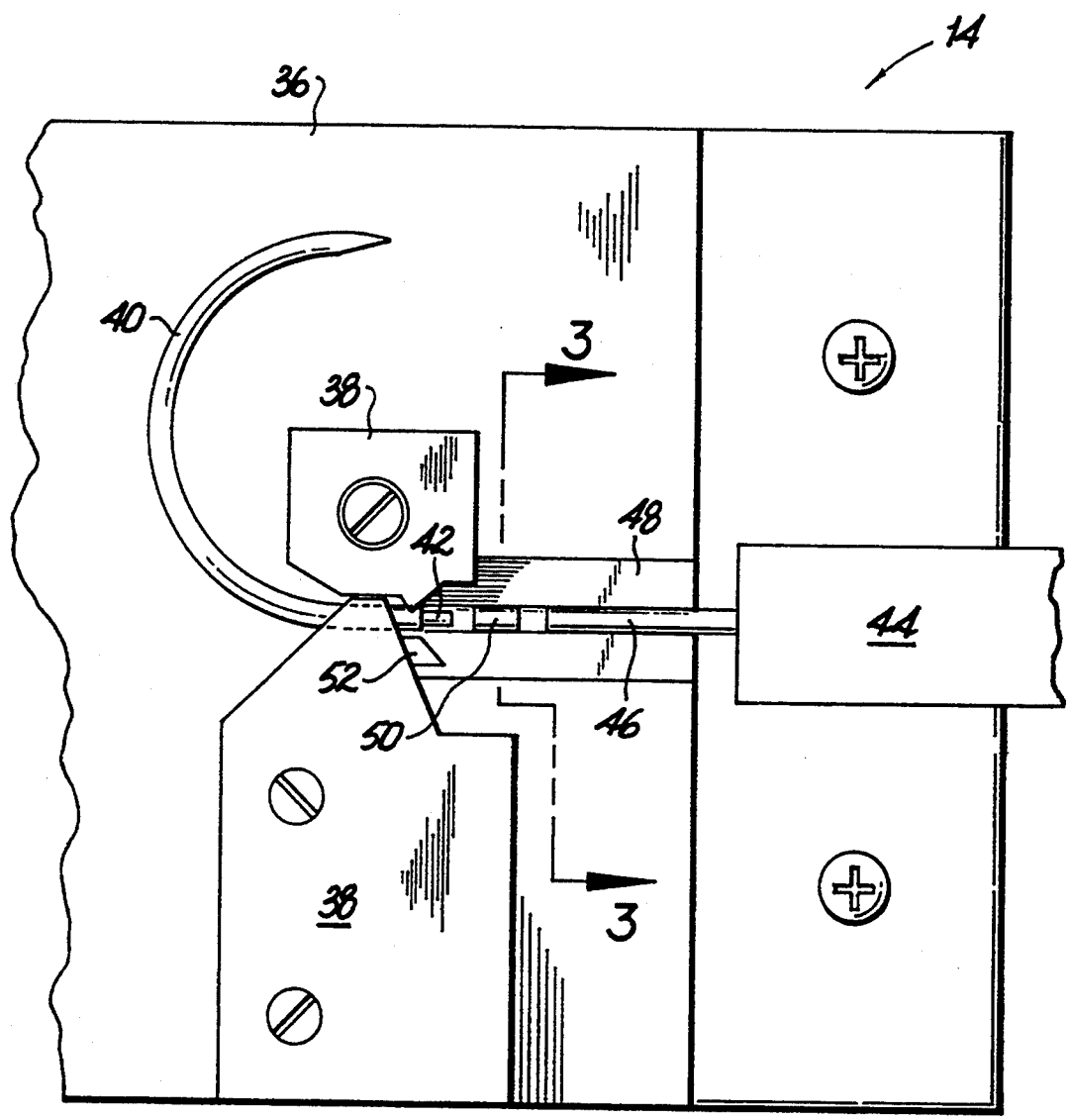
FIG. 2 illustrates an enlarged top plan view of the apparatus for securing a heat shrinkable tubing member to the shank of a needle according to the present invention.
Figure 3:
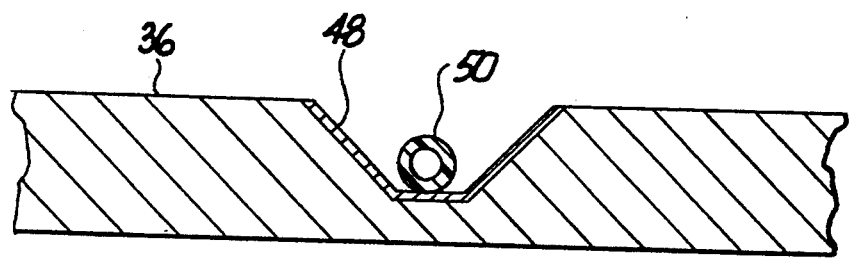
FIG. 3 illustrates a cross-sectional view along lines 3—3 of FIG. 2 showing the heat shrinkable tubing prior to securement to the shank of the needle.
Figure 4:
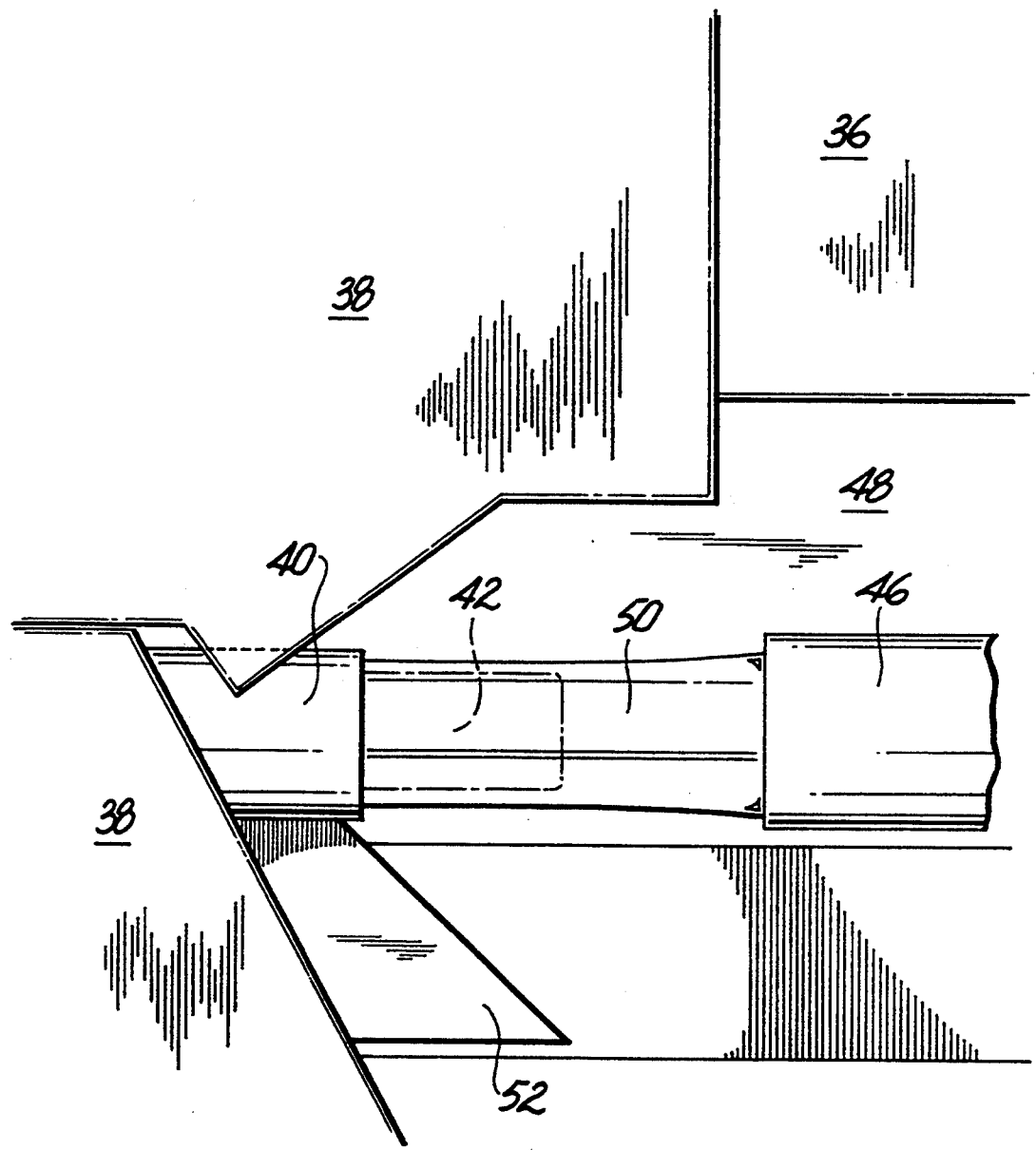
FIG. 4 illustrates a magnified view of the preferred apparatus of the present invention in which the heat shrink tubing is being secured to the shank of the needle.

FIG. 2 illustrates an enlarged view of securing apparatus 14 showing a needle 40 prior to the securing of a length of heat shrinkable tubing 50 to shank 42 of needle 40. Securing apparatus 14 includes a mounting platform, preferably constructed of ceramic block 36, on which needle 40 is placed. Needle 40 is held in position by needle holding device 38, which aligns shank 42 for the application of heat shrinkable tubing 50. After needle 40 is secured in place, heat shrinkable tubing 50 is placed adjacent shank 42 in beveled trough 48 which is positioned to align heat shrink tubing 50 with shank 42. A solenoid 44 is then activated, which extends piston 46 to contact an end of heat shrinkable tubing 50 to force tubing 50 onto shank 42. Solenoid 44 may alternately comprise a pneumatic piston which contacts tubing 50. While tubing 50 is held in place by piston 46, electrode 52 is activated and pivots to engage the shank end of needle 40 to conductively heat shank 42. Heating shank 42 causes heat shrink tubing 50 to shrink about shank 42 from the inside out and secures tubing 50 to shank 42, as block 36 and needle holding device 38 serve as a heat sink. As best seen in FIG. 4, electrode 52 contacts needle 40 and causes only the shank end of heat shrinkable tubing 50 to shrink about shank 42. The end of heat shrink tubing 50 remains essentially unchanged, providing for the insertion of a suture thread as will be described below. FIG. 3 illustrates the positioning of heat shrink tubing 50 within trough 48.

After heat shrink tubing 50 shrinks about shank 42, electrode 52 is pivoted away from needle 40, allowing needle 40 to cool briefly before piston 46 is retracted. At this time, needle holding mechanism 38 releases needle 40 so that the next needle may be fit with the heat shrink tubing.

Figure 5:
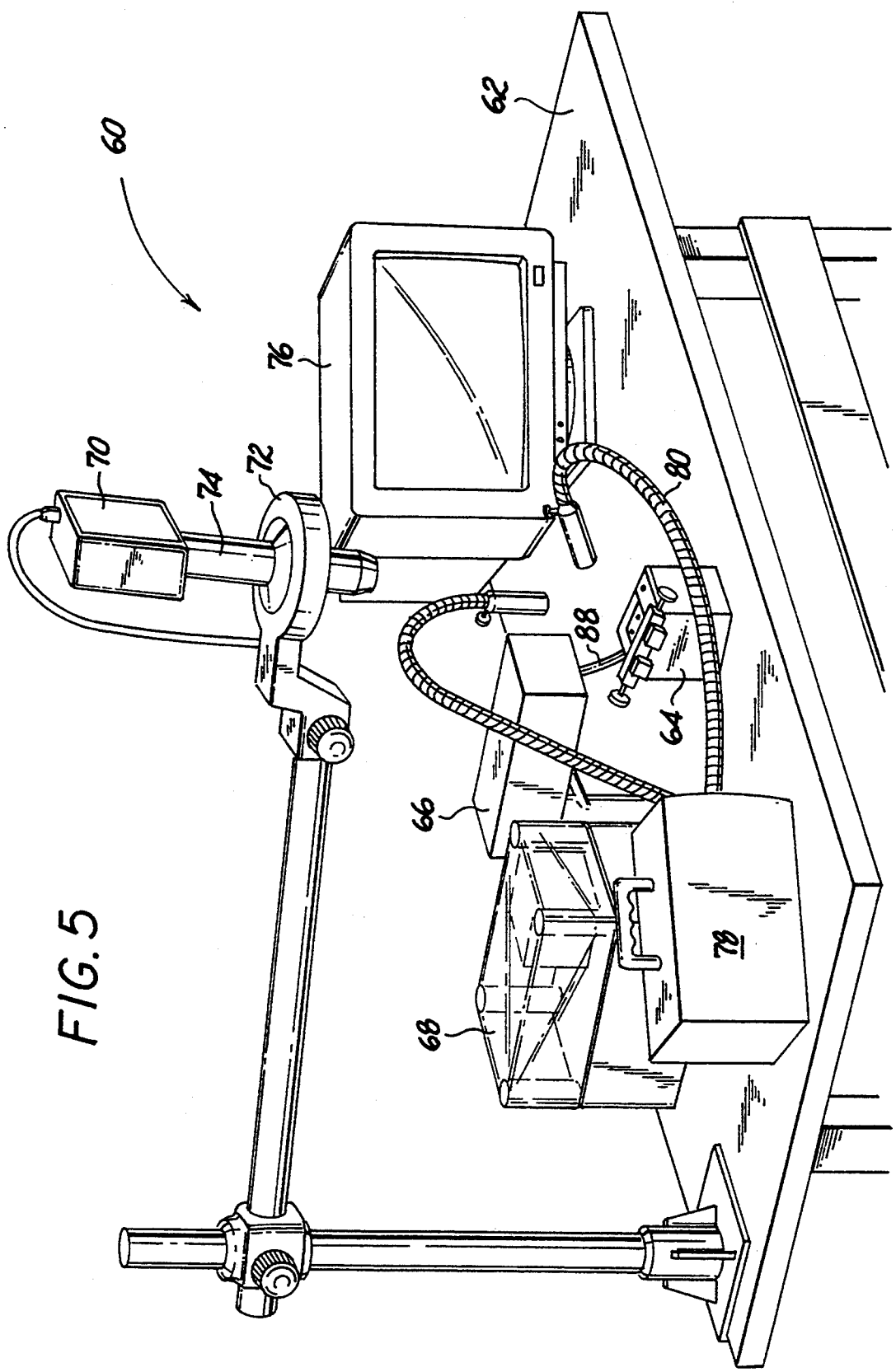
FIG. 5 illustrates the second embodiment of the work station utilizing the apparatus of the present invention.

FIG. 5 illustrates an alternate embodiment of the work station 60 for securing a heat shrinkable tube to the shank end of a needle. Work station 60 is similar to work station 10 of FIG. 1, except primarily for the provision of a different type of heat source. Work station 60, like work station 10, is set up to be manned by an operator and is positioned on a bench or table 62. A securing apparatus 64 is provided and a control connector 66 controls securing apparatus 64. A control terminal 68 is provided to monitor temperature and duration of the application of heat. A video camera 70 is provided and is secured to a mounting bracket 72 so that lens system 74 is positioned over securing apparatus 64. As described above, lens system 74 in video camera 70 provides a magnified image of the work area at securing apparatus 64, and displays such an image on video monitor 76 for the operator's benefit. A light source 78 is provided to illuminate the work area through the provision of telescopic arms 80.

Figure 6:
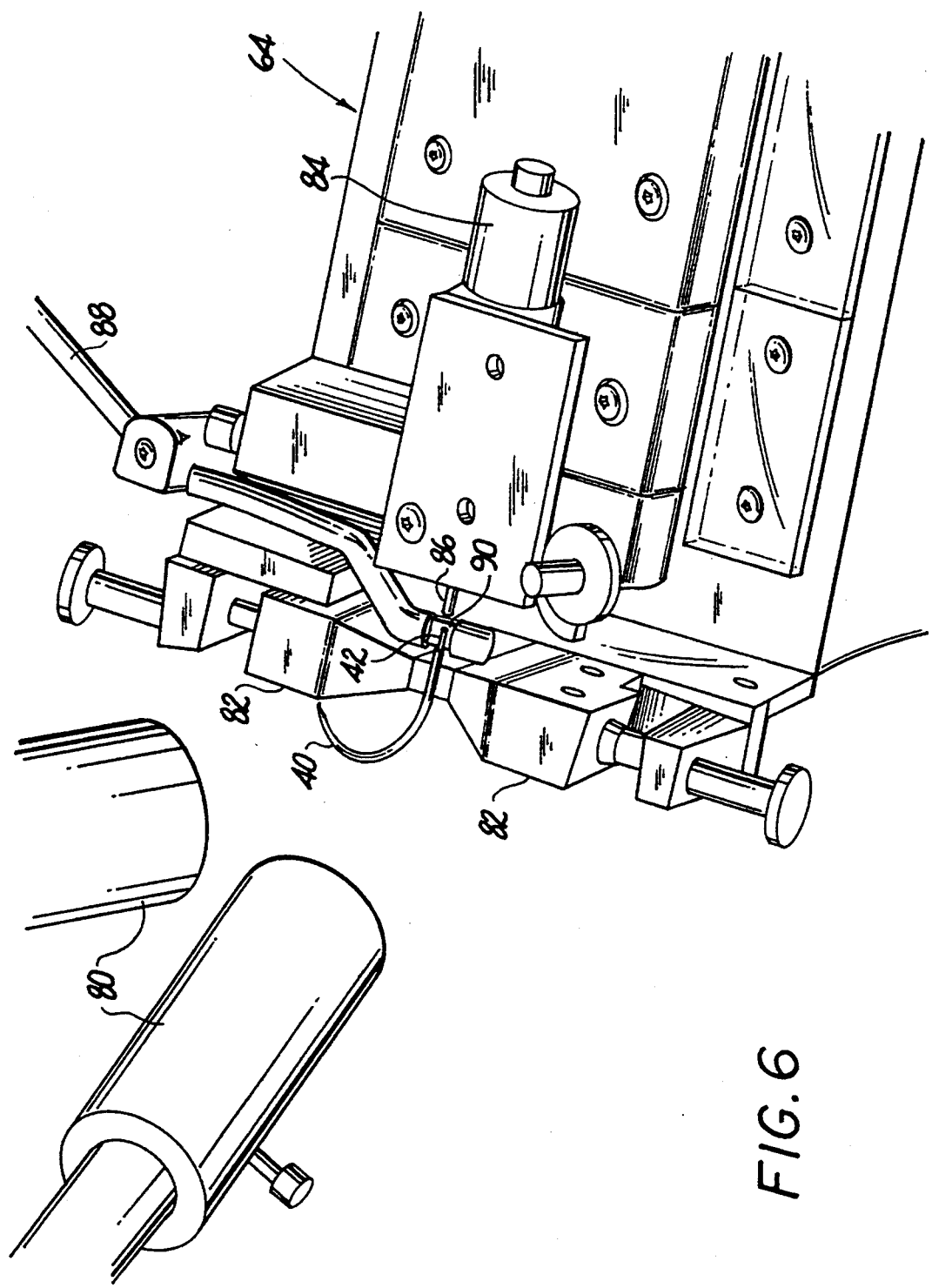
FIG. 6 illustrates an enlarged top perspective view of the apparatus of FIG. 5.

Turning to FIG. 6, there is illustrated an enlarged view of the securing apparatus 64 of FIG. 5. Needle holders 82 are provided for securing a needle 40 in place during the securing process for securing a heat shrinkable tube to the needle shank 42. Light arms 80 are positioned over the work area to illuminate the area and provide a clearer image on the video monitor 76.

After needle 40 is secured in place by needle holders 82, the operator positions a piece of heat shrink tubing (not shown) over shank 42, and then activates solenoid 84 to fire piston 86 to hold the piece of shrink tubing over the shank, similar to that described above in relation to FIG. 2. With piston 86 holding the heat shrink tubing in place, a heat source is activated to provide heated air through heat tube 88 which exits through vent 90 to surround the heat shrink tubing at shank 42. The blast of hot air is preferably short in duration and is hot enough to shrink the tubing about shank 42 without shrinking the tubing at the end which abuts piston 86. In this manner, a suture thread may be inserted into the end of the heat shrink tubing as will be described below.

Figure 7:
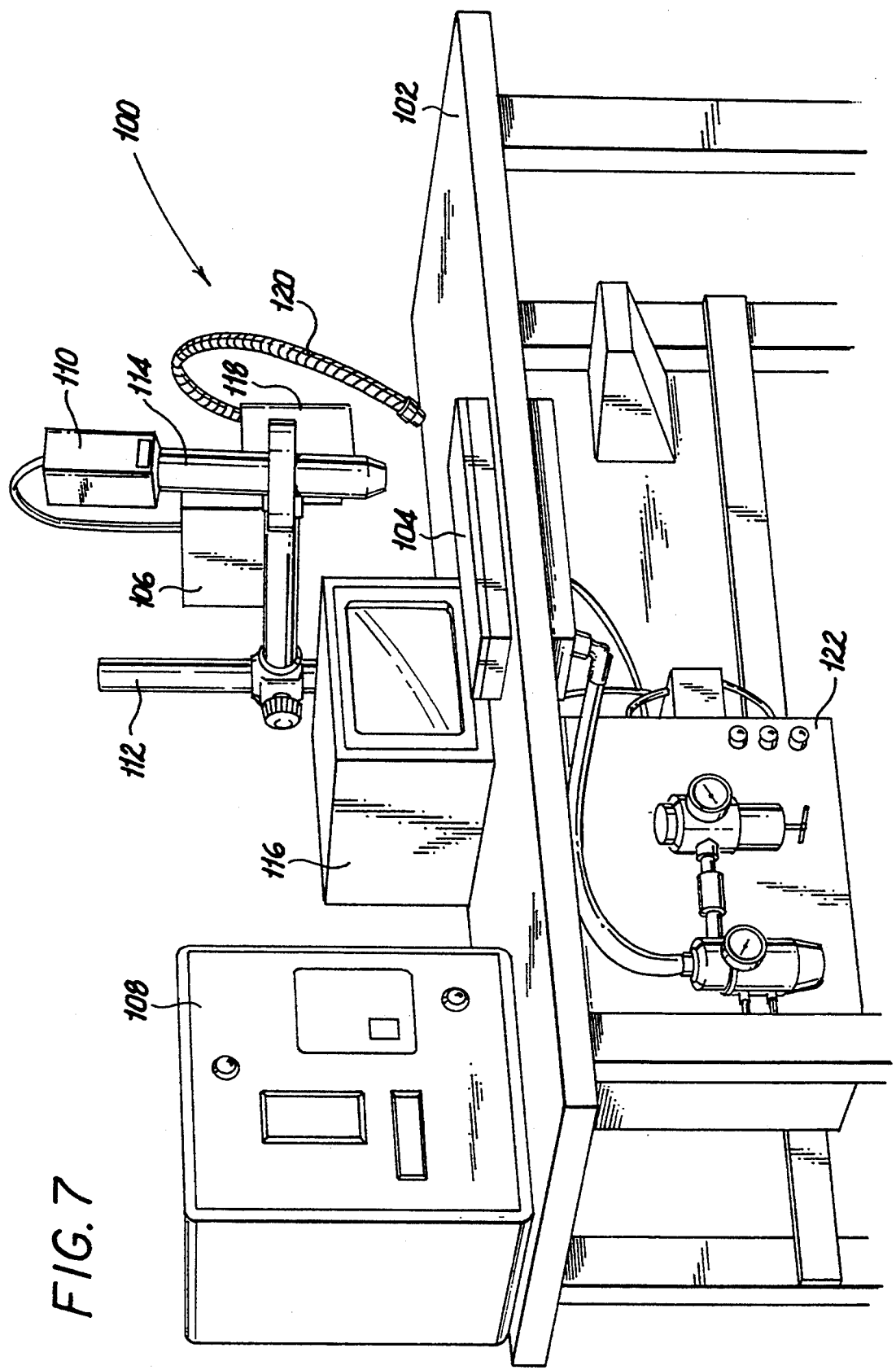
FIG. 7 illustrates a perspective view of a work station for securing suture threads to the shank of a needle having heat shrink tubing already thereon.

Turning now to FIG. 7, there is illustrated work station 100 for securing suture threads to the needle and heat shrink tubing combination. Work station 100, like the previous work stations disclosed above, is assembled on a bench 102 to provide a work area for an operator to secure the suture threads to the heat shrink tubing which is on the needle shank. Work station 100 includes a securing apparatus 104 which is controlled by control terminal 108 through control connector 106. Control terminal 108 comprises a series of temperature gauges and regulators, for maintaining the temperature of the heat source and the duration for which the heat is applied. A video camera 110 is mounted on bracket 112 in a manner similar to that described above, and a lens system 114 is positioned above the work area of securing apparatus 104 to magnify the work area and project its image on video monitor 116. A light source 118 is provided, and telescopic arm 120 illuminates the work area in the vicinity of the lens system 114. FIG. 7 also shows the provision of pressure gauges and a pneumatic system 122 located below the bench 102 which is generally used to control securing apparatus 104. Panel 122 is conventional and may comprise any pneumatic system which is typically controlled by the use of foot pedals which are operated by the operator.

Figure 8A:
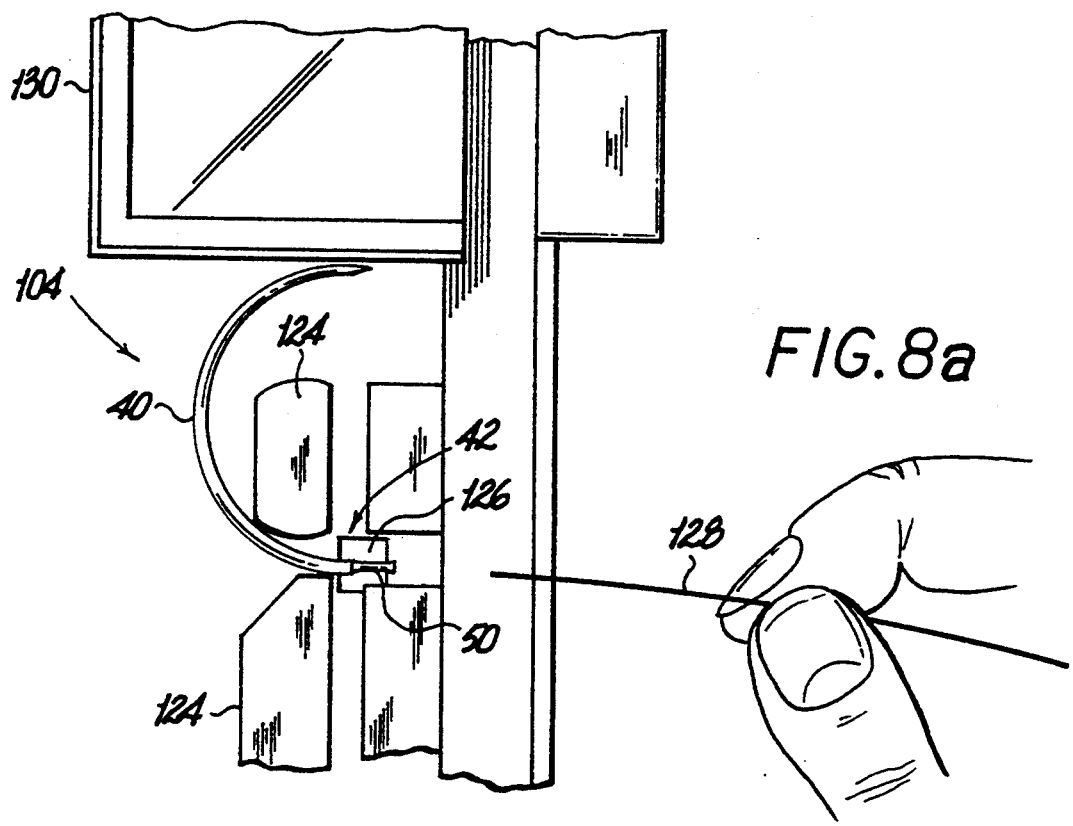
FIGS. 8A through 8C illustrate the securement of a suture thread to the shank of a needle having heat shrink tubing thereon.
Figure 8B:
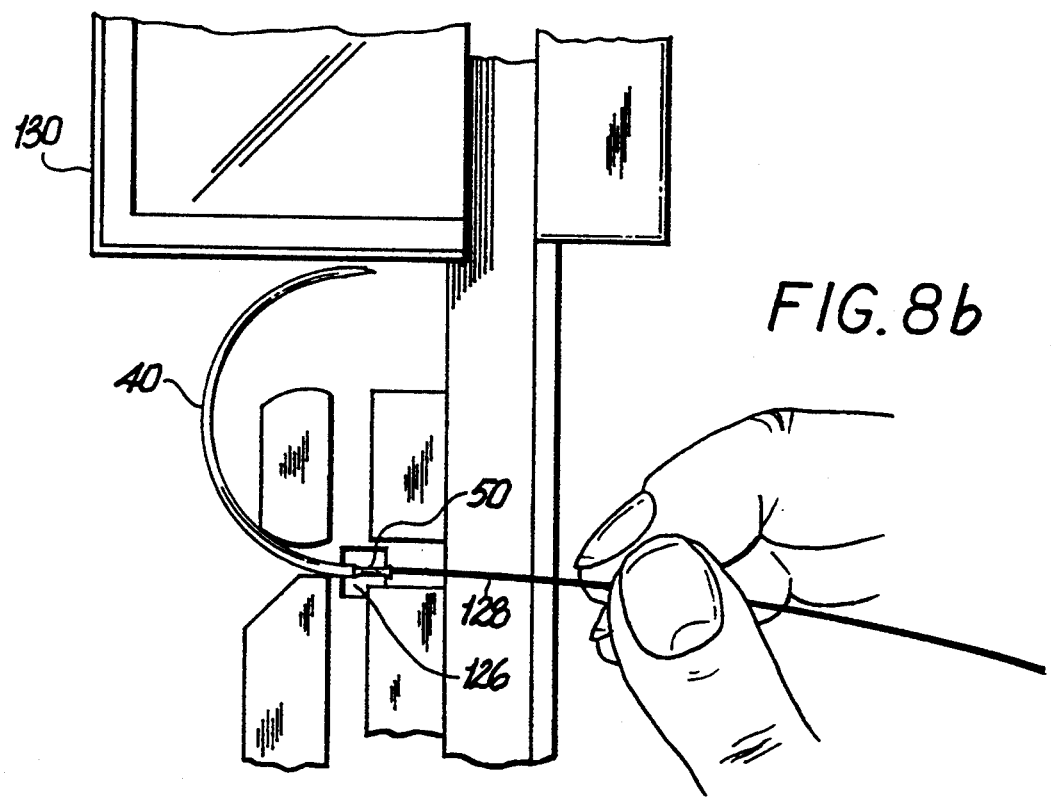
Figure 8C:
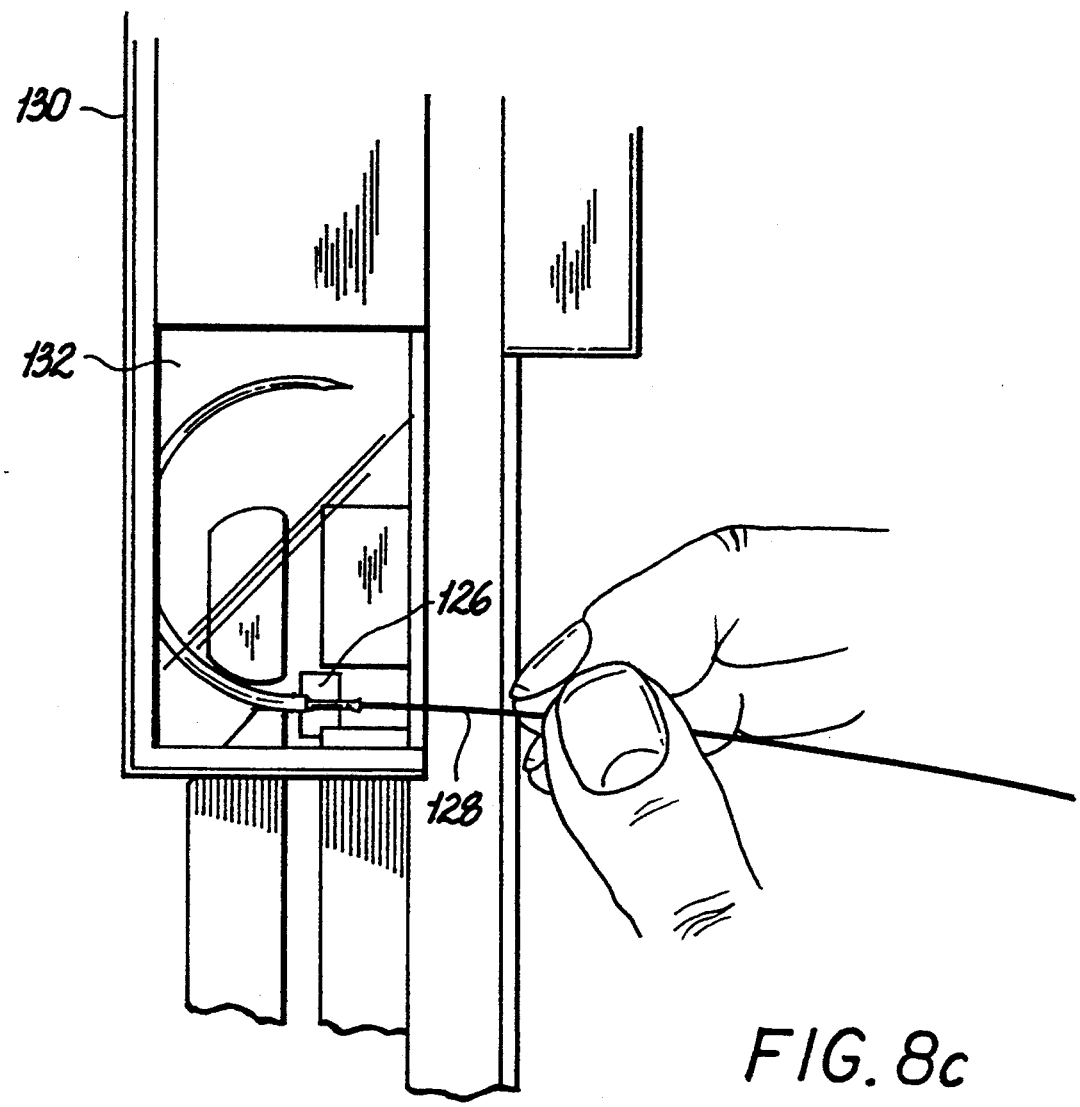

FIGS. 8A through 8C show the steps for securing the suture thread to the needle having a heat shrink tubing member positioned on the shank. An enlarged sectional view of securing apparatus 104 is shown. Needle 40, having heat shrink tubing member 50 secured to shank 42 as described above, is locked into place on securing apparatus 104 through the provision of needle holders 124. The shank and heat shrink tubing are positioned above a heat source opening 126 as shown. As seen in FIG. 8A, the end of heat shrink tubing 50 opposite the needle is somewhat flared outwardly, due to the fact that only the portion of heat shrink tubing 50 which is attached to shank 42 has been shrunk, so that the end of tubing 50 which accepts suture thread 128 is at its original dimensions, thus appearing to be flared as in FIG. 8A. The operator guides suture thread 128 towards heat shrink tubing 50 while viewing the enlarged image on video monitor 116. As best seen in FIG. 8B, suture thread 128 is guided into the end of heat shrink tubing 50 and held in place by the operator. The operator then utilizes the pneumatic system as shown in FIG. 7, to position heat cover 130 over the needle 40, heat opening 126 and the connection point between the shank 42, the heat shrink tubing 50 and the suture thread 128 as best seen in FIG. 8C. Heat cover 130 creates a heat chamber and is provided with a glass window 132 to allow the operator to continue viewing the connection point during the heating procedure. When the cover is in place, heat is vented through opening 126 while cover 130 contains and circulates the heat in the area of the heat shrink tubing to shrink tubing 50 about suture thread 128 to secure the thread to the needle. After the heat is applied for a set duration at a set temperature, which is controlled by control terminal 108, the cover 130 is slid back to its position shown in FIG. 8A. Locking mechanism 124 releases needle 40, and the suture needle apparatus is then removed.

Figure 9:
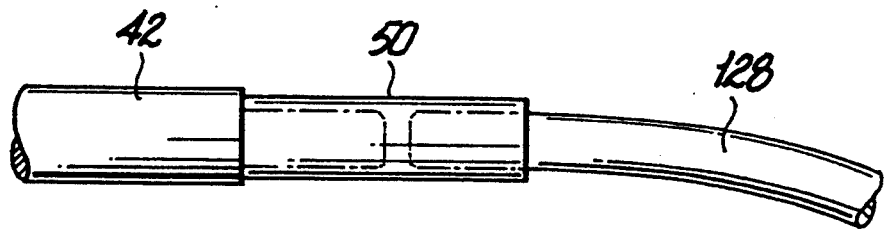
FIG. 9 illustrates the connection between the suture thread and the shank of the needle through the provision of the heat shrink tubing after the suture has been removed from the apparatus of the present invention.

FIG. 9 illustrates the connection point for the suture needle assembly after the heating process is complete. Shank 42 and suture thread 128 are held by heat shrink tubing 50 which has been shrunk about both members to form the connection.

The apparatus for securing suture threads to needle shanks employing heat shrinkable tubing of the present invention provides an efficient and high quality connection to form the suture needle assemblies. Good adhesion is insured between the shank and the heat shrink tubing by uniformly heating the tube about the shank, and likewise the connection between the tube and the suture thread may be accomplished with little degradation to the thread occurring while still providing a high quality securement.

While the invention has been particularly shown and described with reference to the preferred embodiments, it will be understood by those skilled in the art that various modifications and changes in form and detail may be made therein without departing from the scope and spirit of the invention. Modifications such as a single station to allow a single operator to secure the heat shrink tubing to the shank and then to the suture thread may be provided, as well as provisions for simultaneously securing both the suture thread and the needle shank together with the heat shrink tubing. Accordingly, modifications such as those suggested above, but not limited thereto, are to be considered within the scope of the invention.

What is claimed is:

1. Apparatus for forming suture/needle assemblies, said assemblies including a surgical needle and surgical suture thread secured at a shank end of said surgical needle by a length of heat shrinkable tubing, comprising:
   a first station including:
   needle holding means comprising reciprocating means for releasably securing a surgical needle,
   means for positioning a heat shrinkable tubing on a shank of said surgical needle, and
   a heat source for shrinking a portion of said heat shrinkable tubing about said shank; and
   a second station including:
   needle holding means comprising reciprocating means for releasably securing said surgical needle having said heat shrinkable tubing secured thereon,
   a source of surgical suture thread material, said surgical suture thread being positioned within said heat shrinkable tubing at an end of said tubing opposite said shank of said surgical needle, and
   a heat source for shrinking said heat shrinkable tubing about said surgical suture thread to secure said surgical suture thread to said needle shank to form said suture/needle assembly.

2. Apparatus according to claim 1, wherein said first and second stations include control means for controlling the temperature and duration of the application of heat from each of said heat sources.

3. Apparatus according to claim 2, wherein said control means comprises a computer program which controls said heat source and said needle holding means, said needle holding means releasing said surgical needle after a predetermined time period following application of heat from said heat source.

4. Apparatus according to claim 1, wherein said first and second stations include magnification means for magnifying and viewing a work area at each of said stations.

5. Apparatus according to claim 4, wherein said magnification means comprises a video system, said video system including a camera, a lens system and a video monitor for viewing said magnified work area.

6. Apparatus according to claim 4, wherein said magnification means comprises a microscope positioned adjacent said work area for viewing said work area under magnification.

7. Apparatus according to claim 4, wherein said work area comprises an area including said needle holding means, said surgical needle, said heat shrink tubing, said positioning means and said heat source.

8. Apparatus according to claim 1, wherein said heat source at said first station comprises a pivotable electrode which contacts said surgical needle adjacent said shank for heating said shank to shrink said heat shrinkable tubing about said shank.

9. Apparatus according to claim 1, wherein said heat source at said first station comprises a source of hot air, said source including a nozzle for concentrating said hot air onto an area corresponding to said portion of said heat shrinkable tubing overlapping said shank.

10. Apparatus according to claim 1, wherein said heat source at said first station shrinks said tubing only, about said shank, such than an end of said tubing remote from said shank substantially maintains a pre-heated shape and dimension.

11. Apparatus according to claim 1, wherein said first station heat source applies heat at a higher temperature than said second station heat source.

12. Apparatus according to claim 1, wherein said first and second stations are bench-mounted.

13. Apparatus for forming suture/needle assemblies said assemblies including a surgical needle and surgical suture thread secured at a shank end of said surgical needle by a length of heat shrinkable tubing, comprising:
   a first station including:
   needle holding means for releasably securing a surgical needle,
   means for positioning a heat shrinkable tubing on a shank of said surgical needle, and
   a heat source for shrinking a portion of said heat shrinkable tubing about said shank; and
   a second station including:
   needle holding means for releasably securing said surgical needle having said heat shrinkable tubing secured thereon, said needle holding means being pneumatically controlled,
   a source of surgical suture thread material, said surgical suture thread being positioned within said heat shrinkable tubing at an end of said tubing opposite said shank of said surgical needle, and
   a heat source for shrinking a heat shrinkable tubing about a shank surgical suture thread to secure said surgical suture thread to said needle shank to form said suture/needle assembly.

14. Apparatus for forming suture/needle assemblies, said assemblies including a surgical needle and surgical suture thread secured at a shank end of said surgical needle by a length of heat shrinkable tubing, comprising:

a first station including;
needle holding means for releasably securing a surgical needle,
means for positioning said heat shrinkable tubing on said shank of said surgical needle, said positioning means comprising a piston which abuts an end of said heat shrinkable tubing to urge said tubing onto said shank, and
a heat source for shrinking a portion of said heat shrinkable tubing about said shank; and
a second station including;
needle holding means for releasably securing said surgical needle having heat shrinkable tubing secured thereon,
a source of surgical suture thread material said surgical suture thread being positioned within said heat shrinkable tubing at an end of said tubing opposite said shank of said surgical needle, and
a heat source for shrinking said heat shrinkable tubing about said surgical suture thread to secure said surgical suture thread to said needle shank to form said suture/needle assembly.

15. Apparatus according to claim 14, wherein said piston is pneumatically controlled.

16. Apparatus for forming suture/needle assemblies said assemblies including a surgical needle and surgical suture thread secured at a shank end of said surgical needle by a length of heat shrinkable tubing, comprising:

a first station including:
needle holding means for releasably securing a surgical needle,
means for positioning a heat shrinkable tubing on a shank of said surgical needle, said positioning means comprising a solenoid having a movable core, said core urging said heat shrinkable tubing onto said shank, and
a heat source for shrinking a portion of said heat shrinkable tubing about said shank; and
a second station including:
needle holding means for releasably securing said surgical needle having said heat shrinkable tubing secured thereon,
a source of surgical suture thread material, said surgical suture thread being positioned within said heat shrinkable tubing at an end of said tubing opposite said shank of said surgical needle, and
a heat source for shrinking said heat shrinkable tubing about said surgical suture thread to secure said surgical suture thread to said needle shank to form said suture/needle assembly.

17. Apparatus for forming suture/needle assemblies, said assemblies including a surgical needle and surgical suture thread secured at a shank end of said surgical needle by a length of heat shrinkable tubing, comprising:

a first station including:
needle holding means for releasably securing a surgical needle,
means for positioning said heat shrinkable tubing on said shank of said surgical needle, said positioning means comprising a beveled trough for aligning said heat shrinkable tubing with said shank and a piston which abuts an end of said tubing and urges said tubing over said shank, and
a heat source for shrinking a portion of said heat shrinkable tubing about said shank; and
a second station including;
needle holding means for releasably securing said surgical needle having said heat shrinkable tubing secured thereon,
a source of surgical suture thread material, said surgical suture thread being positioned within said he at shrinkable tubing at an end of raid tubing opposite said shank of said surgical needle, and
a heat source for shrinking said heat shrinkable tubing about said surgical suture thread to secure said surgical suture thread to said needle shank to form said suture/needle assembly.

18. Apparatus for forming suture/needle assemblies, said assemblies including a surgical needle and surgical suture thread secured at a shank end of said surgical needle by a length of heat shrinkable tubing, comprising:

a first station including:
needle holding means for releasably securing a surgical needle,
means for positioning said heat shrinkable tubing on said shank of said surgical needle, and
a heat source for shrinking a portion of said heat shrinkable tubing about said shank; and
a second station including;
needle holding means for releasably securing said surgical needle having said heat shrinkable tubing secured thereon,
a source of surgical suture thread material, said surgical suture thread being positioned within said heat shrinkable tubing at an end of said tubing opposite said shank of said surgical needle, and
a source of hot air for shrinking said heat shrinkable tubing about said surgical suture thread to secure said surgical suture thread to said surgical needle shank to form said suture/needle assembly,
wherein said hot air source further includes a heat chamber for enclosing said surgical suture thread, said heat shrink tubing and said shank end to circulate and distribute said hot air about the connection of said suture thread and heat shrink tubing to shrink said tubing about said surgical suture thread.

19. Apparatus according to claim 18, wherein said heat chamber comprises a pneumatically controlled glass cover which reciprocatingly slides and extends over said connection of said surgical thread, said tubing and said shank.

20. Apparatus for preparing surgical needles for incorporation into suture/needle assemblies, said surgical needles having a pointed end and a shank end comprising:

needle holding means for releasably securing a surgical needles:
means for positioning it portion of a length of heat shrink tubing over a shank end of said surgical needle said positioning means comprising a beveled trough for aligning said heat shrink tubing with said shank and a piston which urges said tubing over said shank; and
a heat source for shrinking said portion of heat shrink tubing about said shank end of said surgical needle.

21. Apparatus for preparing surgical needles for incorporation into suture/needle assemblies, said surgical needles having a pointed end and a shank end, comprising:

needle holding means comprising reciprocatingly means for releasably securing a surgical needles;

means for positioning a portion of a length of heat shrink tubing over a shank end of said surgical needle; and a heat source for shrinking said portion of heat shrink tubing about said shank end of said surgical needle.

22. Apparatus according to claim 21, further comprising viewing means for magnifying and displaying a work area which includes said needle holding means, said positioning means, and said heat source.

23. Apparatus according to claim 21, further comprising control means for controlling temperature and duration of application of said heat source.

24. Apparatus according to claim 21, wherein said heat source comprises a pivotable electrode which contacts said surgical needle adjacent said shank end to heat said shank to shrink said tubing about said shank.

25. Apparatus according to claim 21, wherein said heat source comprises a hot air source, said hot air source including a concentrator member for directing and distributing said hot air at said shank end to shrink said portion of tubing about said shank.

26. Apparatus according to claim 21, wherein said needle holding means further comprises a heat sink to ensure heating of said shank end of said needle only.

27. Apparatus for preparing surgical needles for incorporation into suture/needle assemblies, said surgical needles having a pointed end and a shank end, comprising:

needle holding means for releasably securing a surgical needles;

means for positioning a portion of a length of heat shrink tubing over a shank end of said surgical needle said positioning means comprising a piston, said piston abutting an end of said shrink tubing to position said tubing over said shank end of said surgical needle: and a heat source for shrinking said portion of heat shrink tubing about said shank end of said surgical needle.

28. Apparatus according to claim 27, wherein said piston comprises a movable core of a solenoid.

29. Apparatus for forming surgical suture/needle assemblies said suture/needle assemblies including a surgical needle having a pointed end and a shank end, said shank end having a length of heat shrinkable tubing secured thereon and extending outwardly from said shank, said apparatus comprising:

needle holding means for releasably securing a surgical needle;

a source of surgical suture thread material said material being insertable into an end of said heat shrinkable tubing remote from said shank end of said surgical needle;

a heat source: and a heat chamber means for containing heat from said heat source and circulating heat about said heat shrinkable tubing to shrink said tubing about said surgical suture thread to form said suture/needle assembly, wherein said heat chamber means comprises a slidable glass cover which slides over said needle shank, said heat shrinkable tubing, said surgical suture thread positioned in said heat shrinkable tubing and said heat source prior to application of heat from said heat source.

30. Apparatus for forming surgical suture/needle assemblies, said suture/needle assemblies including a surgical needle having a pointed end and a shank end, said shank end having a length of heat shrinkable tubing secured thereon and extending outwardly from said shank, said apparatus comprising:

needle holding means for releasably securing a surgical needle;

a source of surgical suture thread material, said material being insertable into an end of said heat shrinkable tubing remote from said shank end of said surgical needle;

a heat source; and heat chamber means slidably moveable with respect to said heat shrinkable tubing for containing heat from said heat source and circulating heat about a portion of said heat shrinkable tubing to shrink said tubing about said surgical suture thread to form said suture/needle assembly.

31. Apparatus according to claim 30, further comprising control means for controlling temperature and duration of application of heat from said heat source.

32. Apparatus according to claim 30, further comprising viewing means for magnifying and displaying a work area which includes said needle holding means, said surgical suture thread material, said heat source and said heat chamber means.

33. Apparatus according to claim 30, wherein said needle holding means positions said shank and heat shrink tubing adjacent said heat source.

34. Apparatus according to claim 30, wherein said heat source comprises a source of hot air.

35. Apparatus according to claim 30, wherein said suture/needle assembly comprising a surgical needle having a pointed end and a shank end, a length of surgical suture thread material, and a length of heat shrink tubing shrunk about said shank and an end of said surgical thread to secure said surgical thread to said shank.

36. A method for forming surgical suture/needle assemblies, said suture/needle assemblies including a surgical needle having a surgical suture thread attached thereto through the provision of a length of heat shrinkable tubing, said method comprising the steps of:

securing a surgical needle in a needle holding device;

positioning a length of heat shrinkable tubing adjacent a shank end of said surgical needle;

urging a portion of said tubing over said shank end;

applying a source of heat to said shank end of said surgical needle to shrink said portion of said tubing about said shank;

removing said heat source;

positioning said surgical suture thread into an end of said heat shrinkable tubing remote from said shank;

applying a source of heat by circulating the heat to said tubing positioned over said surgical suture thread, thereby shrinking shrink said tubing over said surgical suture thread; and releasing said surgical needle and surgical suture thread assembly from said needle holding device.

37. A method for forming surgical suture/needle assemblies, said suture/needle assemblies including a surgical needle having a surgical suture thread attached thereto through the provision of a length of heat shrinkable tubing, said method comprising the steps of:

securing a surgical needle in a needle holding device;

positioning a length of heat shrinkable tubing adjacent a shank end of said surgical needle:

urging a portion of said tubing over said shank end;

applying a source of heat to said shank end of said surgical needle to shrink said portion of said tubing about said shank;

removing said heat source;

positioning said surgical suture thread into an end of said heat shrinkable tubing remote from said shank;

covering said needle shank, said heat shrinkable tubing and said surgical suture thread with a slidable glass cover prior to the application of heat to circulate the heat for shrinking said tubing over said surgical suture thread;

applying a source of heat to said tubing to shrink said tubing over said surgical suture thread; and releasing said surgical needle and surgical suture thread assembly from said needle holding device.

38. The method according to claim 37, wherein said suture/needle assembly comprising a surgical needle having a pointed end and a shank end, a length of surgical suture thread material, and a length of heat shrink tubing shrunk about said shank and an end of said surgical thread to secure said surgical thread to said shank.

* * * * *